US010519323B2

(12) United States Patent
Zhang et al.

(10) Patent No.: US 10,519,323 B2
(45) Date of Patent: Dec. 31, 2019

(54) ANTIMICROBIAL COATINGS

(71) Applicant: AGENCY FOR SCIENCE, TECHNOLOGY AND RESEARCH, Singapore (SG)

(72) Inventors: Yugen Zhang, Singapore (SG); Yuan Yuan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/769,709

(22) PCT Filed: Oct. 19, 2016

(86) PCT No.: PCT/SG2016/050509
§ 371 (c)(1),
(2) Date: Apr. 19, 2018

(87) PCT Pub. No.: WO2017/069702
PCT Pub. Date: Apr. 27, 2017

(65) Prior Publication Data
US 2018/0320000 A1 Nov. 8, 2018

(30) Foreign Application Priority Data
Oct. 19, 2015 (SG) .......................... 10201508654T

(51) Int. Cl.
C09D 5/14 (2006.01)
A01N 25/34 (2006.01)
A01N 43/50 (2006.01)
A61K 31/4164 (2006.01)
A61K 47/02 (2006.01)
C07F 3/06 (2006.01)
C07D 233/58 (2006.01)
B82Y 30/00 (2011.01)
C01B 39/32 (2006.01)

(52) U.S. Cl.
CPC .............. C09D 5/14 (2013.01); A01N 25/34 (2013.01); A01N 43/50 (2013.01); A61K 31/4164 (2013.01); A61K 47/02 (2013.01); C07D 233/58 (2013.01); C07F 3/06 (2013.01); B82Y 30/00 (2013.01); C01B 39/32 (2013.01)

(58) Field of Classification Search
CPC ........ A01N 25/34; A01N 43/50; A01N 59/16; A61K 31/4164; A61K 47/02; C01B 39/32; C07D 233/02; C07D 233/58; C07F 3/06; C09D 5/14
See application file for complete search history.

(56) References Cited

U.S. PATENT DOCUMENTS 9,527,872 B2 * 12/2016 Thompson .............. C07F 3/003
2012/0237697 A1 9/2012 Abbasi et al.
2015/0273755 A1 10/2015 Yee et al.

FOREIGN PATENT DOCUMENTS

| CN | 103638979 A | 3/2014 |
| CN | 104538298 A | 4/2015 |
| CN | 104855380 A | 8/2015 |
| WO | WO 2012/020214 A2 | 2/2012 |
| WO | 2015031956 A1 | 3/2015 |
| WO | WO 2015/031956 A1 | 3/2015 |
| WO | WO 2015/048442 A1 | 4/2015 |

OTHER PUBLICATIONS

IP Office of Singapore—Notification of Transmittal of the International Search Report & the Written Opinion of the International Searching Authority, or the Declaration, with the International Search Report & Written Opinion dated Dec. 23, 2016 for International Application No. PCT/SG2016/050509 (17 pgs).
Chapter II Demand with Article 34 Amendment filed Jun. 19, 2017 with the IP Office of Singapore for International Application No. PCT/SG2016/050509 (22 pgs).
Li, Y.S. et al. "Controllable Synthesis of Metal-Organic Frameworks: From MOF Nanorods to Oriented MOF Membranes." Advanced Materials, vol. 22, No. 30, Jun. 8, 2010, pp. 3322-3326.
Zhong, Z., et al., "Oriented two-dimensional zeolitic imidazolate framework-L membranes and their gas permeation properties." J. of Materials Chemistry A, Issue 30, 2015, pp. 15715-15722.
Liu, Q., et al., "Direct conversion of two-dimensional ZIF-L film to porous ZnO nano-sheet film and its performance as photoanode in dye-sensitized solar cell." Microporous and Mesoporous Materials, vol. 194, Aug. 2014, pp. 1-7.
IP Office of Singapore—International Preliminary Report on Patentability for International Application No. PCT/SG2016/050509, 23 pgs. (dated Nov. 15, 2017).
Bell, Graham, et al.; "Arming the Enemy: The Evolution of Resistance to Self-Proteins" Microbiology, 149 (2003); 9 pages.
Gao, Ping, et al.; "Recent Advances in Materials for Extended-Release Antibiotic Delivery System" The Journal of Antibiotics 64 (2011); 10 pages.

(Continued)

Primary Examiner — Anthony J Green
(74) Attorney, Agent, or Firm — Womble Bond Dickinson (US) LLP

(57) ABSTRACT

A coating comprising a metal-organic framework, wherein the metal-organic framework having a zeolitic structure comprising at least one multivalent metal species and at least one organic ligand (such as zeolitic imidazolate framework (ZIF)). Said coating has a topography comprising an array of projections, and each projection having at least one tapered distal end. There is also provided a method of coating substrates with the disclosed coating and use of said coating as a disinfectant, an antiseptic, or an antibiotic. Such use is possible because the tapered distal end of the disclosed zeolitic structure exerting higher pressure on any microbial cell that comes into contact with the disclosed coating, thereby piercing through the cell membrane more easily, causing cell deformation and lysis.

20 Claims, 7 Drawing Sheets

(56) References Cited

OTHER PUBLICATIONS

Humphreys, Hilary, et al.; "Self-Disinfecting and Microbiocide-Impregnated Surfaces and Fabrics: What Potential in Interrupting the Spread of Healthcare-Associated Infection?" Healthcare Epidemiology (2014); 6 pages.

Extended European Search Report of European Patent Application No. EP16857896; search report completed on Jul. 12, 2018; 18 pages.

Aguado, Sonia, et al.; Antimicrobial Activity Cobalt Imidazolate Metal-Organic Frameworks; Chemosphere 113 (2014) 5 pages.

Banerjee, Rahul, et al.; " High-Throughput Synthesis of Zeolitic Imidazolate Frameworks and Application to CO2 Capture"; Science, vol. 319 (2008); 6 pages.

Betard, Angelique, et al.;"Metal-Organic Framework Thin Films: From Fundamentals to Applications"; Chemical Reviews (2012); 29 pages.

Chen, Rizhi, et al.; "A Two-Dimensional Zeolitic Imidazolate Framework With a Cushion-Shaped Cavity for CO2 Adsorption"; Chem. Commun. (2013); 3 pages.

Cohen Stuart, Martien A., et al.; "Emerging Applications of Stimuli-Responsive Polymer Materials"; Nature Materials vol. 9 (2010); 13 pages.

Demessence, Aude, et al.; "Adsorption Properties in High Optical Quality NanoZIF-8 Thin Films with Tunable Thickness"; J Mater. Chem. (2010); 6 pages.

Diu, Ting, et al.; "Cicada-Inspired Cell Instructive Nanopatterned Arrays "; Scientific Reports (2014); 7 pages.

Donlan, Rodney M., et al.; "Biofilms: Survival Mechanisms of Clinically Relevant Microorganisms"; Clinical Microbiology Reviews (2002); 27 pages.

Eddaoudi, Mohamed, et al.; "Modular Chemistry: Secondary Building Units as a Basis for Design of Highly Porous and Robust Metal-Organic Carboxylate Frameworks"; Account of Chemical Research (2001); 12 pages.

Erer, Hakan, et al.; "Synthesis, Spectroscopic, Thermal Studies, Antimicrobial Activities and Crystal Structures of Co(II), Ni(II) and Zn(II)-Orotate Complexes With 2-Methylimidazole" Polyhedron 28 (2009); 7 pages.

Fink, Lori J., et al.; "Antisepsis/Disinfection/Sterilization"; Poster Abstracts/American Journal of Infection Control 41 (2013); 2 pages.

Gerber, Lukas C., et al.; "Incorporation of Penicillin-Producing Fungi into Living Materials to Provide Chemically Active and Antibiotic-Releasing Surfaces"; Angew. Chem. Int. Ed (2012); 4 pages.

Hasan, Jafar, et al.; "Selective Bactericidal Activity of Nanopatterned Superhydrophobic Cicada Psaltoda Claripennis Wing Surfaces"; Appl Microbiol Biotechnol (2013); 6 pages.

Horcajada, Patricia, et al.; "Metal-Organic Frameworks in Biomedicine"; Chemical Reviews (2012); 37 pages.

Huang, Aisheng, et al.; "Bicontinuous Zeolitic Imidazolate Framework ZIP-8@GO Membrane with Enhanced Hydrogen Selectivity"; Journal of the American Chemical Society (2014); 4 pages.

Ivanova, Elena P., et al.; "Natural Bactericidal Surfaces: Mechanical Rupture of Pseudomonas Aeruginos Cells by Cicada Winds"; Small (2012); 6 pages.

Ivanova, Elena P., et al.; "Bactericidal Activity of Black Silicon" Nature Communications (2013); 7 pages.

Kim, Sohee, et al.; "Nanostructured Multifunctional Surface with Antireflective and Antimicrobial Characteristics"ACS Applied Materials and Interfaces (2015); 6 pages.

Komnatnyy, Vitaly V., et al.; "Bacteria-Triggered Release of Antimicrobial Agent"; Angew. Chem. Int. Ed (2014): 3 pages.

Kugel, Alex, et al.; "Antimicrobial Coatings Produced by "Tethering" Biocides to the Coating Matrix: A Comprehensive Review"; Progress in Organic Coatings 73 (2011); 31 pages.

Lai, Kwan Kew, et al.; "Use of Silver-Hydogel Urinary Catheters on the Incidence of Catheter-Associated Urinary Tract Infections in Hospitalized Patients"; AJIC vol. 30 No. 4 (2002); 5 pages.

Li, Jian-Rong, et al.; "Metal-Organic Frameworks for Separations"Chem. Rev. (2012); 64 pages.

Nugent, Patrick, et al.; "Porous Materials With Optimal Adsorption Thermodynamics and Kinetics for CO2 Separation"; Nature vol. 495 (2013); 5 pages.

Park, Kyo Sung, et al.; "Exceptional Chemical and Thermal Stability of Zeolitic Imidazolate Frameworks"; PNS vol. 103 No. 27 (2006); 6 pages.

Pham, Vy T., et al.; "Nanotopography as a Trigger for the Microscale, Autogenous and Passive Lysis of Erythrocytes"; Journal of Materials Chemistry 2 (2014); 9 pages.

Phan, Anh, et al.; Synthesis, Structure and Carbon Dioxide Capture Properties of Zeolitic Imidazolate Frameworks; Accounts of Chemical Research, vol. 43 No. 1 (2010); 10 pages.

Pogodin, Sergey, et al.; "Biophysical Model of Bacterial Cell Interactions with Nanopatterned Cicada Wing Surfaces". Biophysical Journal vol. 104 (2013); 6 pages.

Qiu, Shilun, et al.; "Metal-Organic Framework Membranes: From Synthesis to Separation Application" Chem. Soc. Rev (2014); 25 pages.

Rieter, William J., et al.; "Surface Modification and Funotionalization of Nanoscale Metal-Organic Frameworks for Controlled Release and Luminescence Sensing"; J. Am. Chem. Soc. (2007); 2 pages.

Sakata, Yoko, et al.; "Shape-Memory Nanopores Induced in Coordination Frameworks by Crystal Downsizing" Science vol. 339 (2013); 5 pages.

Sanz, Ruy, et al.; "UV-Black Rutile TiO2: An Antireflective Photocatalytic Nanostructure"Journal of Applied Physics 117 (2015); 9 pages.

Tello, Alfredo, et al., "Selective Pressure of Antibiotics Pollution on Bacteria of Importance to Public Health" Environmental Health Perspectives, vol. 120 No. 8 (2012); 7 pages.

Tiller, Joerg C., et al.; "Designing Surfaces That Kill Bacteria on Contact " PNAS, vol. 98 No. 11 (2001); 5 pages.

Yao, Jianfeng, et al.; "High-Yield Synthesis of Zeolitic Imidazolate Frameworks From Stoichicmetric Metal and Ligand Precursor Aqueous Solutions at Room Temperature" CrystEngComm 15 (2013); 6 pages.

Yu, Dongbo, et al.; "Precisely Tailoring ZIF-67 Nanostructures from Cobalt Carbonate Hydroxide Nanowire Arrays: Toward High-Performance Battery-Type Electrodes" Journal of Material Chemistry A. 3 (2015); 7 pages.

Zamani, Azam, et al.; "Synthesis, Characterization Spectrophotometrics Investigation, Structural Study, and Antibacterial Activities of a Series of New Zinc(II) Complexes"; Journal of Coordination Chemistry, vol. 67, No. 10 (2014); 13 pages.

Nowlin, Kyle, et al.; "Adhesion-Dependent Rupturing of Saccharomyces Cerevisiae on Biological Antimicrobial Nanostructured Surfaces"; J. R. Soc. Interface (2014); 12 pages.

Weber, David J., et al.; "Self-Disinfecting Surfaces: Review of Current Methodologies and Future Prospects"; American Journal of Infection Control 41 (2013); 5 pages.

* cited by examiner

[Fig. 1]
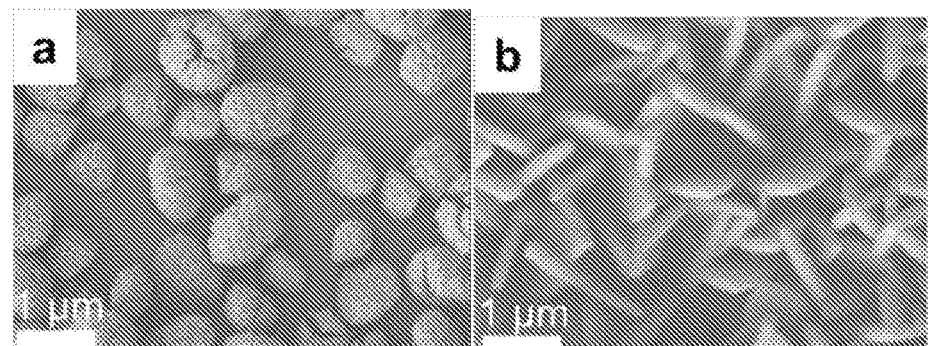
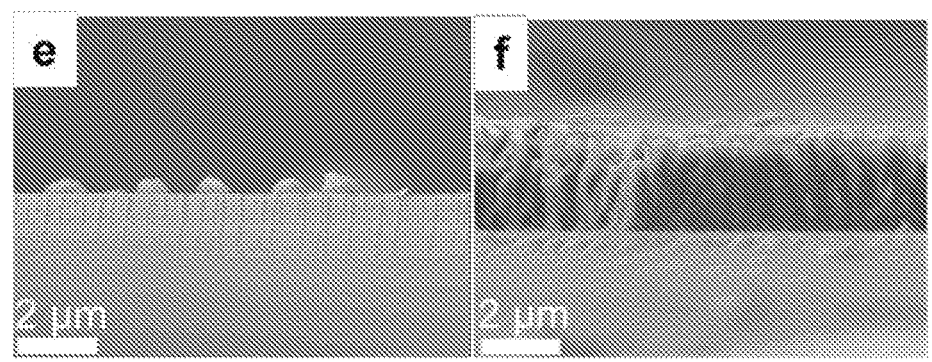
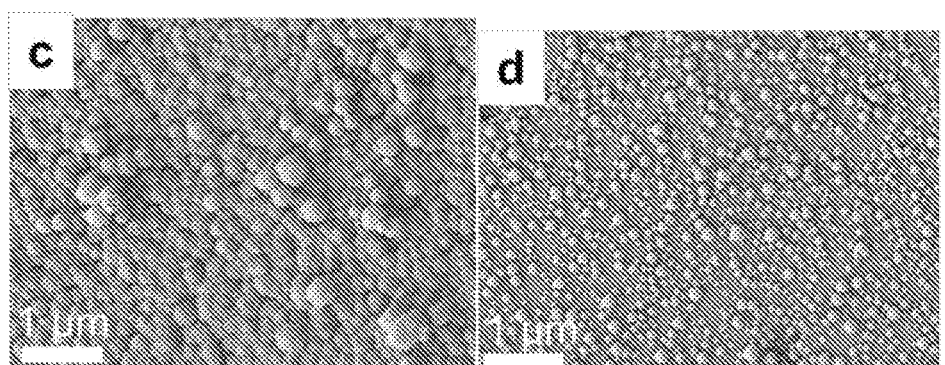
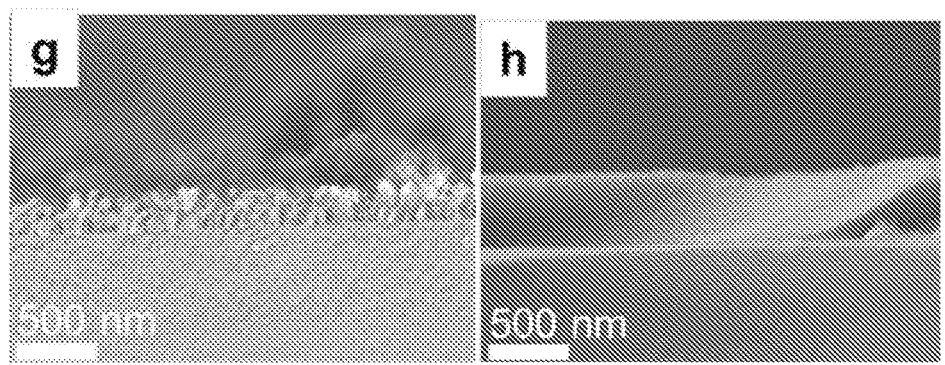

[Fig. 1] cont'd
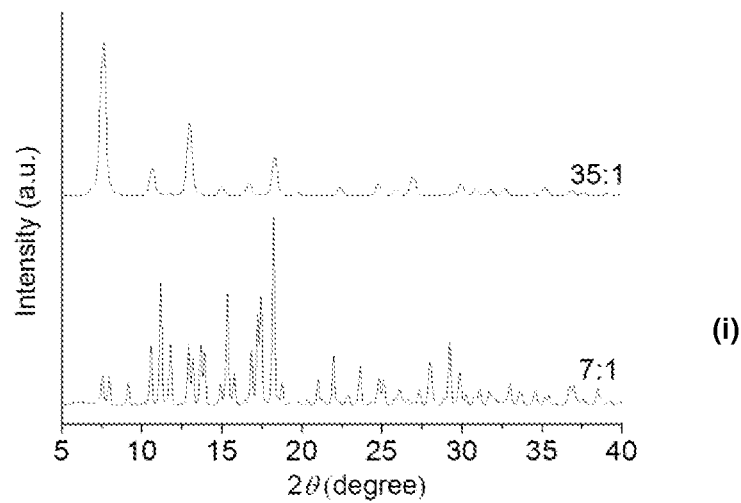
(i)
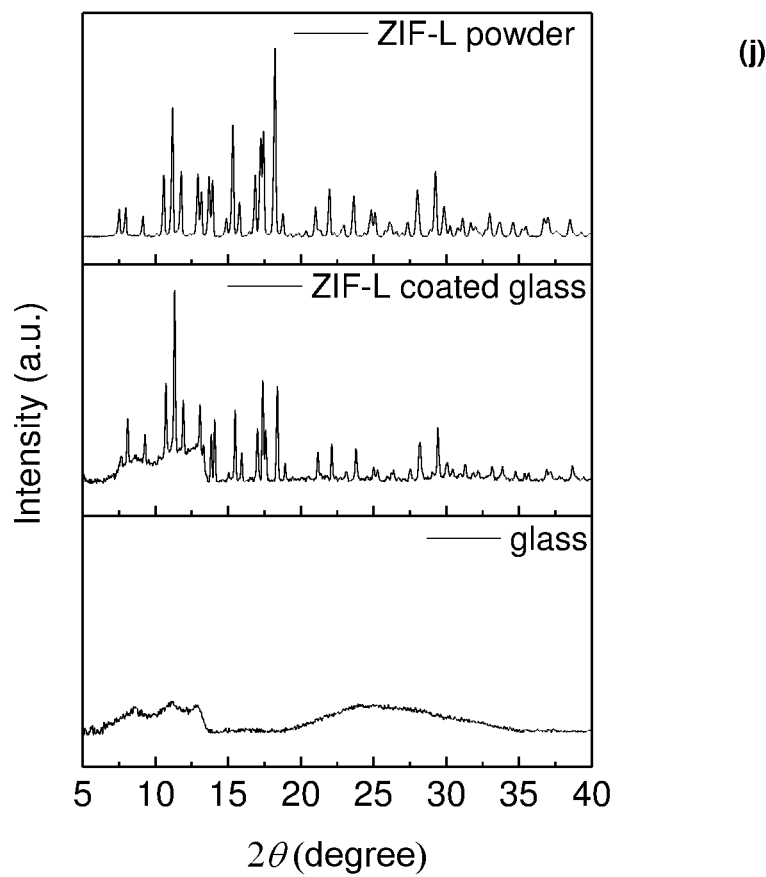
(j)

[Fig. 2]
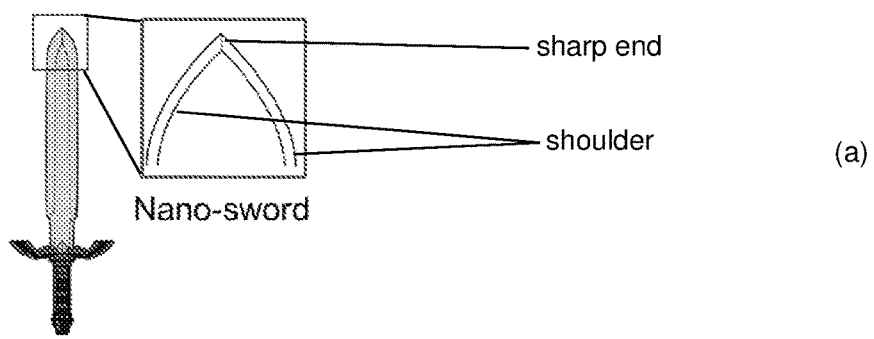
(a)
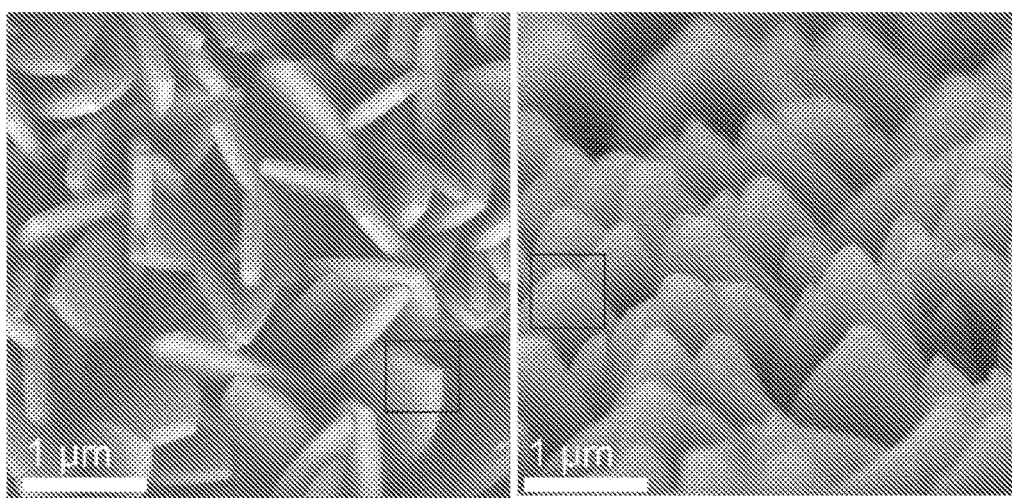
(b)

[Fig. 3]
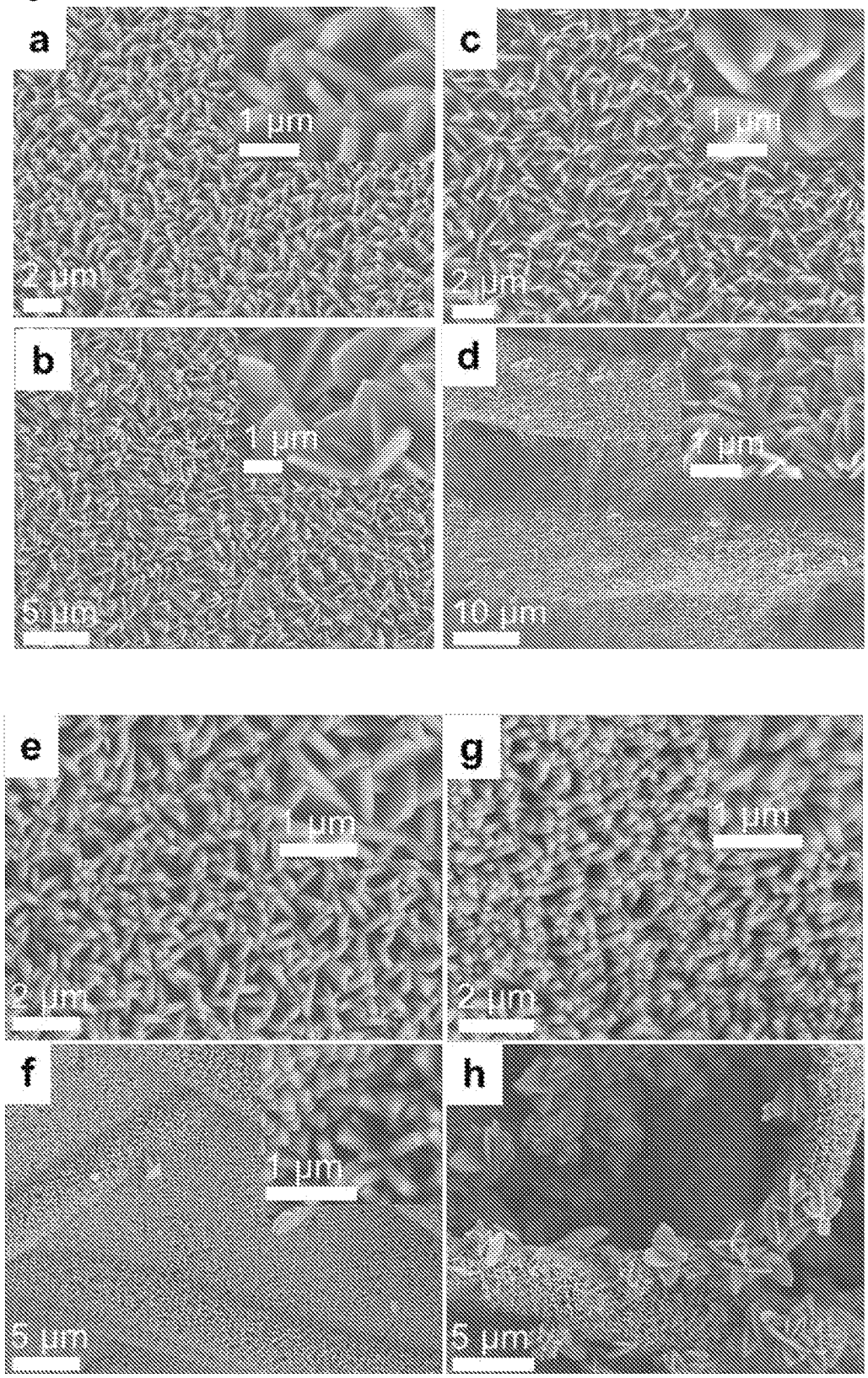

[Fig. 4]
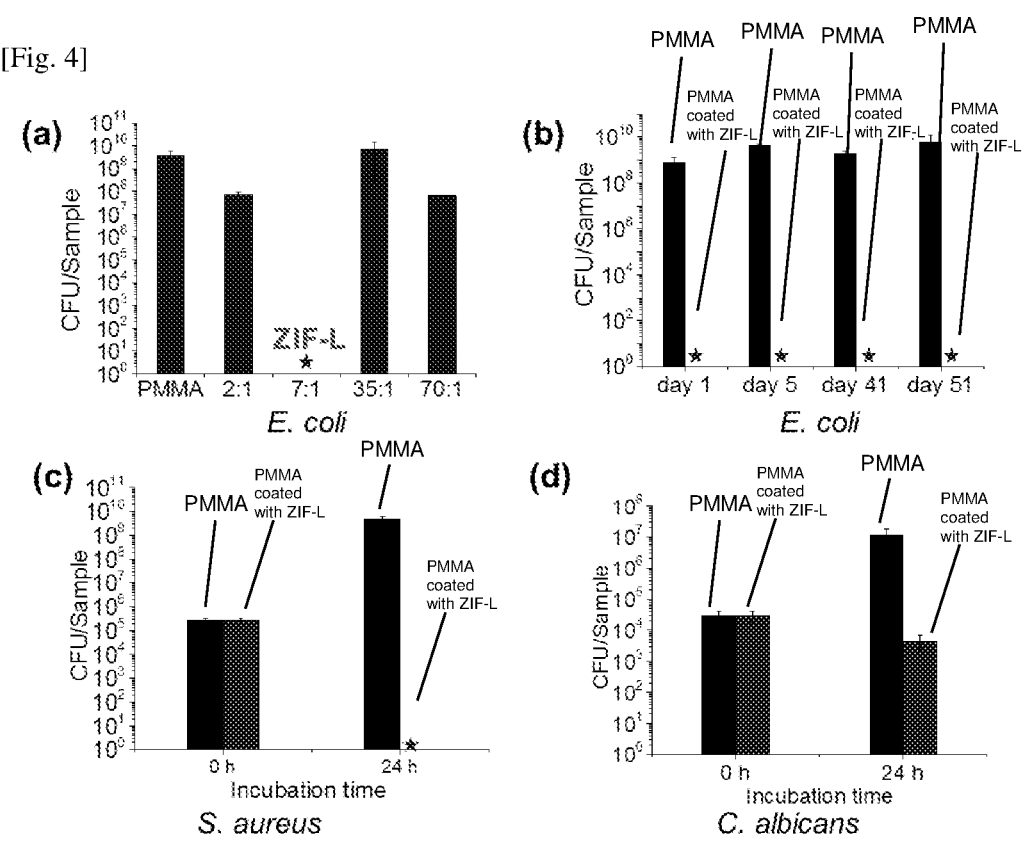

[Fig. 5]
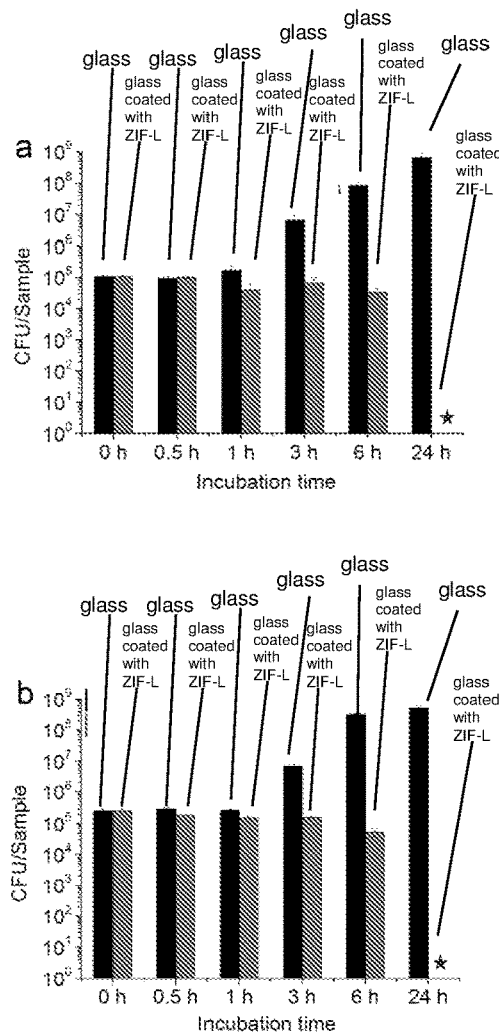
[Fig. 6]
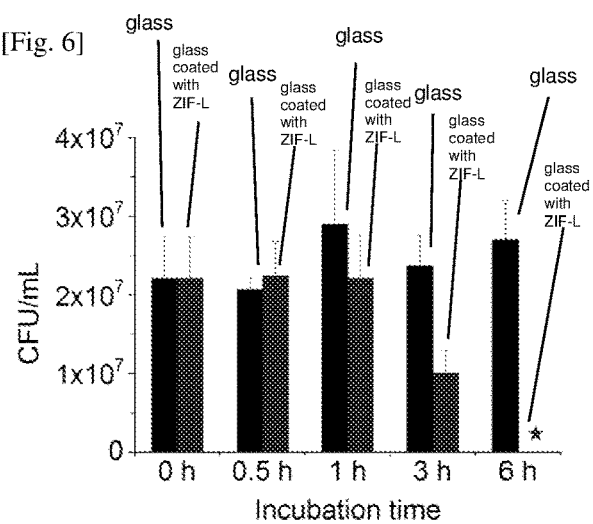

[Fig. 7]
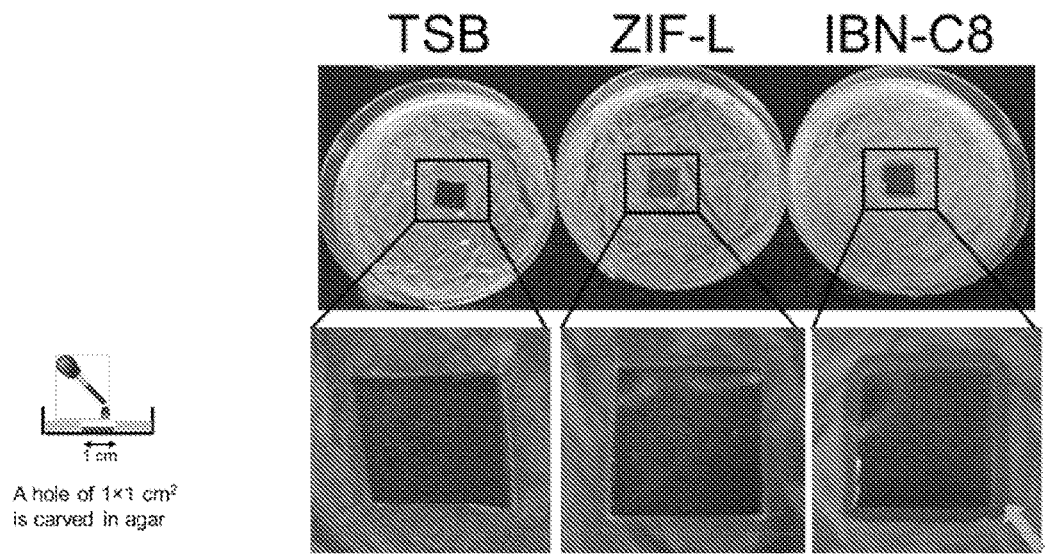
[Fig. 8]
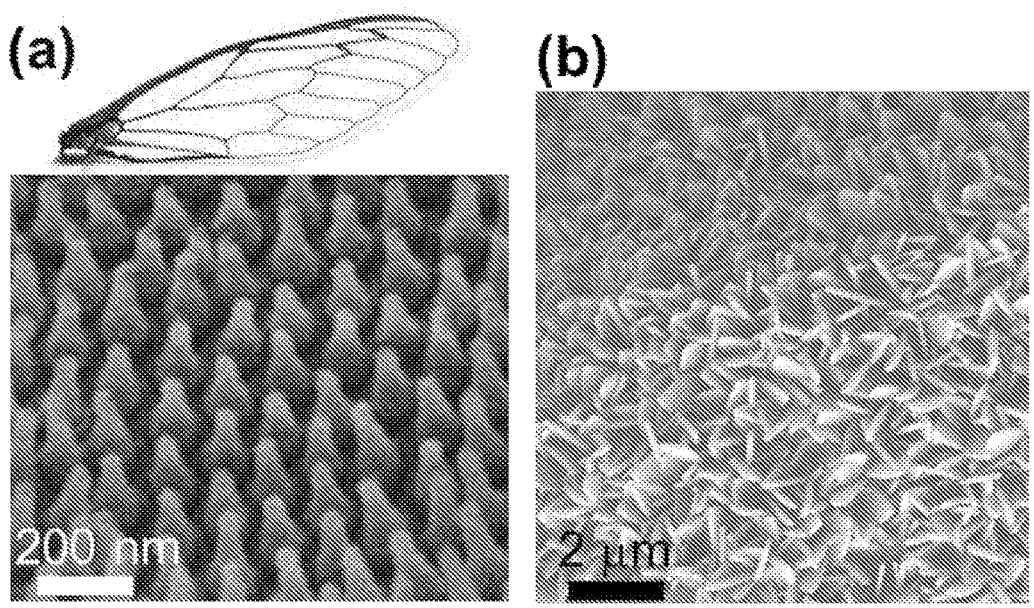

US 10,519,323 B2

ANTIMICROBIAL COATINGS

CROSS-REFERENCE TO RELATED APPLICATIONS

This patent application is a U.S. National Phase application under 35 U.S.C. § 371 of International Application No. PCT/SG2016/050509, filed 19 Oct. 2016, entitled ANITIMICROBIAL COATINGS, which claims priority to Singapore Patent Application No. 10201508654T, filed 19 Oct. 2015.

TECHNICAL FIELD

The present invention generally relates to coatings that possess bactericidal or antimicrobial activity. The present invention also relates to a method of coating substrates with the disclosed coating and uses of the disclosed coating or coated surface.

BACKGROUND ART

Infectious diseases and the increasing threat of worldwide pandemics have underscored the importance of antibiotics and hygiene. Microbial infection is also one of the most serious concerns for many commercial applications, such as medical devices and hospital surfaces, textiles, food packaging, children's toys, electrical appliances, and dental surgery equipment. Intensive efforts have been devoted to create self-disinfecting and microbicide surfaces, mainly achieved by coating microbicides onto surfaces to biochemically reduce the infectivity of microbes. However, critical challenges still remain at this point such as growing drug resistance to the microbicide agents, low microbial killing efficacy and poor long-term stability of the coated surfaces.

It was recently disclosed that a biological strategy relying on a physical mechanism of action rather than a biochemical mechanism of action provided a promising solution to bacterial growth. In this disclosure, it was discovered that cicada wing surfaces are covered with dense patterns of nanoscale pillar structures, which are cylindrical and have rounded ends, and prevent bacterial growth by rupturing adhered microbial cells. It was also proven that a purely physical interaction between synthetic nanopatterns, such as black silicon surfaces, and cells also results in cell deformation and massive lysis without the need for additional external chemicals or mechanical means to aid in microbial killing. This discovery of a physical mechanism of action opens up a great opportunity for the development of innovative microbicide surface technologies which are clean and safe, require no external chemicals and have no microbial resistance issues. However, there are no existing technologies that can create such cell-destructive surfaces in an efficient and simple way.

As mentioned above, nanostructures on surfaces of black silicon and $TiO_2$ have demonstrated microbicide properties. These surface nano-patterns were generated by a top-down approach on specific materials, which becomes very challenging when the patterns go down to the nanometer scale. Accordingly, these surfaces tend to be prohibitively expensive and the method of synthesis is limited to certain types of materials.

On the other hand, metal organic frameworks (MOFs) construct their defined nano-patterns via a bottom-up (self-assembly) approach with metal species and polyfunctional organic linkers. This approach has been used for growing MOF membranes or films on the surfaces of various substrates. Therefore, the quest for integrating MOFs into substrate-based applications like sensing, separation and catalysis has attracted increasing attention in the past decade. This interest is correlated to the unique properties of MOFs, such as the mild reaction conditions for synthesis and their proven chemical and thermal stability. However, the bottom-up approach has not been applied to the preparation of biomimicry surfaces that demonstrate microbicide properties.

There is therefore a need to provide a surface or coating demonstrating microbicide properties that overcomes, or at least ameliorates, one or more of the disadvantages described above.

There is also a need to provide a general and scalable method of making patterned surfaces with high microbicide activity.

SUMMARY OF INVENTION

According to a first aspect, there is provided a coating comprising a metal-organic framework, the metal-organic framework having a zeolitic structure comprising at least one multivalent metal species and at least one organic ligand, the coating having a topography comprising an array of projections, and each projection having at least one tapered distal end.

Advantageously, the disclosed coating possesses bactericidal or antimicrobial properties. The bactericidal or antimicrobial action may utilize a physical mechanism for killing microorganisms, rather than a chemical or biochemical mechanism, thereby advantageously avoiding the development of microbial or drug resistance. Without being bound by theory, it is postulated that the topography of the disclosed coating (in particular its array of tapered or pointed projections) is capable of damaging or puncturing cell membranes or cell walls of microorganisms which come into contact with a surface coated with the coating described herein. It is further postulated that the topography of the coating as described herein may substantially or completely prevent cell adhesion on the coated surface.

Further advantageously, the disclosed coating may be deposited on or coupled to a variety of substrate surfaces, which can be smooth, flat or uneven, or hydrophilic or hydrophobic, to confer bactericidal or antimicrobial properties on the surface.

According to a second aspect, there is provided a method of coating a substrate with a layer of metal-organic framework having a zeolitic structure, the method comprising the steps of:
  a. providing an aqueous solution comprising an organic ligand;
  b. contacting at least a surface of the substrate with the solution; and
  c. reacting the organic ligand with a multivalent metal species to thereby deposit the metal-organic framework layer on the surface of the substrate.

Advantageously, the coating may be assembled or obtained directly or in situ on the substrate surface. Thus, the disclosed coating may be advantageously economical to prepare and may not require sophisticated or expensive equipment.

According to a third aspect, there is provided a method of preparing a disinfectant, antiseptic or an antibiotic, comprising coating a surface of a substrate with a coating as defined herein.

According to a fourth aspect, there is provided the use of a zeolitic imidazolate framework (ZIF) as defined herein in the manufacture of a medicament for disinfection, as an antiseptic, or for sterilization.

Definitions

The following words and terms used herein shall have the meaning indicated:

The term "array" is to be interpreted broadly to refer to multiple numbers of structures distributed within an area and spaced apart. Structures within an array do not have to have the same orientation.

The term "projection" is to be interpreted broadly to refer to a structure that extends outwards from a surface.

The term "tapered distal end" refers to a pointed apex of a structure.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a coating will now be disclosed.

In an embodiment, there is provided a coating comprising a metal-organic framework, said metal-organic framework having a zeolitic structure comprising at least one multivalent metal species and at least one organic ligand, said coating having a topography comprising an array of projections, and each projection having at least one tapered distal end.

Metal-organic frameworks (MOFs) are a class of crystalline compounds that comprise coordination bonds between transition-metal cations and multidentate organic ligands.

Zeolites are similar to MOFs in that zeolites are crystalline solid structures that comprise coordination bonds between silicon, aluminum and oxygen atoms, forming a framework with cavities and channels inside where cations, water and/or small molecules may reside. The term "zeolitic structure" as used in the context of the present invention refers to such a cage-like structure, wherein the aluminum and silicon framework atoms are partly or fully replaced by other multivalent ions, e.g. multivalent metal ions or multidentate organic ligands.

In embodiments of the present disclosure, the multivalent metal species may be transition metal species selected from divalent, trivalent, tetravalent and pentavalent metal ions and mixtures thereof. The multivalent metal species may be selected from the d-block of the Periodic Table of Elements. For example, the multivalent metal species may include Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg or combinations thereof. In other examples, the multivalent metal species may include Al, Si, Ga, In, As, Ge or combinations thereof. In a particular embodiment, the multivalent metal species is selected from Cu, Zn, Ag, Cd, Au, Hg and combinations thereof. In yet another embodiment, the multivalent metal species is Zn. There may be one, two, three, four, five, six, seven, eight, nine or 10 different types of multivalent metal species in the zeolitic structure.

The organic ligand is an organic molecule in which there may be one or multiple sites that enable the binding of said organic ligand to another organic ligand of the same or different type or to the multivalent metal species, thereby resulting in the zeolitic structure. In embodiments, the organic ligand may be monodentate or polydentate, such as bidentate, tridentate, tetradentate, pentadentate or hexadentate. In embodiments, the organic ligand may be an imidazole, an imidazole derivative, an imidazolate or a substituted imidazolate.

A zeolitic structure comprising an imidazole, imidazole derivative, imidazolate or substituted imidazolate ligand(s) is called a zeolitic imidazolate framework (ZIF). Accordingly, the disclosed coating or the disclosed metal-organic framework may comprise a ZIF.

Advantageously, ZIFs are non-toxic, chemically stable and thermally stable up to 200° C. Thus, the disclosed coating is advantageously capable of maintaining its structure and topography at temperatures of below 200° C.

The ZIF may comprise a two-dimensional or three-dimensional structure. The zeolitic imidazolate framework may comprise a multivalent metal species tetrahedrally coordinated with said organic ligand. In other embodiments, the multivalent metal species may be linearly coordinated or trigonally coordinated or octahedrally coordinated or cubic coordinated with said organic ligand.

The coating may comprise one or more layers of ZIF assembled on a substrate surface by reaction between a multivalent metal species and an organic ligand. In other words, a substrate may be coated on its surface with the disclosed coating. Advantageously, the disclosed coating may not require any adhesive to aid in adhering to the substrate surface. Advantageously, the disclosed coating may have superior attachment to supports or substrates. Further advantageously, ZIFs are known to result in continuous and pinhole-free coatings, films or membranes.

Thus, the disclosed metal organic framework may be prepared by contacting a substrate surface with a reaction mixture comprising the organic ligand and the multivalent metal species. The coating may be assembled in situ on a substrate surface that is brought into contact with a reaction mixture comprising a salt solution of the multivalent metal species and a solution comprising an imidazole, imidazole derivative, imidazolate or substituted imidazolate. The assembly of the layers of ZIF may occur in situ to result in the disclosed coating. Advantageously, the disclosed coating may be economical to prepare and may not require sophisticated or expensive equipment.

The self-assembly of multivalent metal species and organic ligands result in patterns and topographies on a substrate surface. Accordingly, due to the plurality of structural possibilities, ZIF crystals may have different shapes, such as a polyhedron shape or a sword or a flake or a leaf-type shape.

The organic ligand may be derived from an imidazole having the following structure:

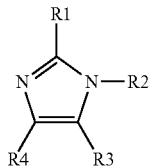

wherein R1 is alkyl, alkenyl, cycloalkyl, or aryl; R2 is H; and each R3 and R4 is independently H, alkyl, alkenyl, cycloalkyl, or aryl; wherein each of R1 to R4 is optionally substituted with halogen, amino, hydroxy, $C_{1-10}$ alkyl, oxo, cyano, nitro, haloalkyl, alkoxy and haloalkoxy.

As used herein, the term "alkyl" refers to linear or branched $C_{1-20}$ alkyl, unless otherwise stated. The alkyl may be methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, undecyl, or dodecyl.

The term "alkenyl" refers to straight chain or branched chain unsaturated aliphatic groups containing at least one carbon-carbon double bond and having from 2 to 20 carbon atoms. The alkenyl may be ethenyl, propenyl, butenyl, 1-butenyl, 2-butenyl, 2-methylpropenyl, 1-pentenyl, 2-pentenyl, 2-methylbut-1-enyl, 3-methylbut-1-enyl, 2-methylbut-2-enyl, 1-hexenyl, 2-hexenyl, 3-hexenyl, 2,2-dimethyl-2-butenyl, 2-methyl-2-hexenyl, 3-methyl-1-pentenyl, or 1,5-hexadienyl.

The term "cycloalkyl" refers to a non-aromatic, mono- or multicyclic ring system comprising about 3 to about 20 carbon atoms. The cycloalkyl may be cyclopropyl, cyclopentyl, cyclohexyl, cycloheptyl, 1-decalinyl, norbornyl, or adamantyl.

The term "aryl" refers to a monovalent or divalent, single, polynuclear, conjugated or fused residues of aromatic hydrocarbons having from 6 to 20 carbon atoms. The aryl may be phenyl, biphenyl, naphthyl, or phenanthrenyl.

As used herein, the term "halogen" refers to fluorine, bromine, chlorine, and iodine. The term "alkoxy" may refer to an —O-alkyl radical. Representative examples of alkoxy include, but are not limited to, methoxy, ethoxy, n-propoxy, isopropoxy, tert-butoxy, and the like. The term "haloalkyl" refers to an alkyl group as described herein wherein one or more of the carbon atoms is covalently bonded to a halogen group. The term "haloalkoxy" shall be construed accordingly.

In an embodiment, the organic ligand is derived from the compound:

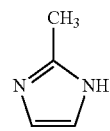

In an embodiment, the organic ligand is 2-methylimidazole.

When the organic ligand is 2-methylimidazole (2-Me-Im) and the multivalent metal specie is Zn, the resultant ZIF crystals may exhibit, for example, either a polyhedron shape or a sword shape having at least one tapered end. The configuration having at least one tapered end is described herein interchangeably as a sword, a flake or a leaf.

The sword-shaped Zn/2-Me-Im ZIF crystal is called ZIF-L, while the polyhedron Zn/2-Me-Im ZIF crystal is called ZIF-8. The sword-shaped ZIF-L crystals project from the substrate surface with the end pointing away from the substrate surface, i.e. the distal end or the apex, being tapered. The tapered distal end makes the sword-shaped crystal structure appear sharp. On the other hand, the distal end of the polyhedron ZIF-8 crystals appears as rounded. Micrographs of the planar ZIF-L crystals and the polyhedron ZIF-8 crystals are shown, respectively, in FIG. 1b and FIG. 1c. Accordingly, the metal-organic framework may have a ZIF-L crystal structure.

The powder of Zn/2-Me-Im ZIF crystal comprising at least one tapered distal end may be characterized by an x-ray diffraction pattern comprising diffraction peaks at 2θ values, wherein the highest peak has a 2θ value of about 15 to 17. In comparison, the powder of Zn/2-Me-Im ZIF crystal comprising rounded distal ends may be characterized by an x-ray diffraction pattern comprising diffraction peaks at 2θ values, wherein the highest peak has a 2θ value of about 7 to 8.

The zeolitic structure may be of an orthorhombic crystal system. In embodiments, the zeolitic structure may be of a bipyramidal point group. In a specific embodiment, the zeolitic structure has a unit cell having a Cmce space group, wherein a is 24.1191(5), b is 17.0604(3) and c is 19.7398(4). These embodiments of zeolitic structure advantageously enable the projection to have at least one tapered or sharp distal end.

It has been discovered herein that zeolitic crystal structures having at least one tapered distal end advantageously demonstrate or possess microbicide activity, in contrast with the zeolitic crystal structures having rounded distal ends which are non-bactericidal.

The zeolitic crystal structure having at least one tapered distal end may cause inhibition or reduction of bacteria at a concentration of less than about 5000 ppm, or less than about 4000 ppm, or less than about 3000 ppm, or about 2500 ppm or 2.5 mg/mL. The zeolitic crystal structure having at least one tapered distal end may cause inhibition or reduction of fungi at a concentration of less than about 5000 ppm, or less than about 4000 ppm, or less than about 3000 ppm, or less than about 2000 ppm, or about 1200 ppm or 1.2 mg/mL. In comparison, the zeolitic crystal structures having rounded distal ends may not cause inhibition or reduction of bacteria and fungi, or may have a minimal inhibitory concentration of about 5000 ppm or higher.

The metal organic framework may be prepared from a reaction mixture comprising a salt solution of the multivalent metal species (M) and a solution comprising an organic ligand. The metal organic framework may be prepared from a reaction mixture comprising a salt solution of the multivalent metal species (M) and a solution comprising an imidazole, imidazole derivative, imidazolate or substituted imidazolate (collectively referred to as imidazole or Im).

The multivalent metal species may be selected from one or several as disclosed herein. The salt solution may comprise a metal halide, a metal sulphate, a metal carbonate, a metal nitrate, a metal chlorate, a metal formate or mixtures thereof. In some embodiments, the salt solution may comprise a divalent metal salt, wherein the metal salt is selected from a salt of Zn, Co, Fe or Cu. In some embodiments, the salt solution may comprise zinc bromide ($ZnBr_2$), zinc chlorate ($Zn(ClO_3)_2$), zinc chloride ($ZnCl_2$), zinc iodide ($ZnI_2$), zinc nitrate ($Zn(NO_3)_2$), zinc sulphate, or mixtures thereof.

The organic ligand may be imidazole or 2-methylimidazole.

The imidazole and the metal species may be provided in a molar ratio of Im:M of around 20:1 to about 4:1. The imidazole and the metal species may be provided in molar ratios selected from 20:1, 19:1, 18:1, 17:1, 16:1, 15:1, 14:1, 13:1, 12:1, 11:1, 10:1, 9:1, 8:1, 7:1, 6:1, 5:1 and 4:1. In an embodiment, the imidazole and the metal species may be provided in a molar ratio of Im:M of about 9:1 to about 5:1. In a preferred embodiment, the imidazole and the metal species may be provided in a molar ratio of Im:M of about 8:1 to about 6:1. Advantageously, when the molar ratio of Im:M is provided within these ranges, a coating may be prepared having the desired topography. Further advantageously, the molar ratio of Im:M as disclosed herein enables the formation of an array of projections, each projection having at least one tapered distal end. Even further advantageously, the formation of projections with pointed apices confers an antimicrobial or bactericidal effect on the coating.

In a most preferred embodiment, the imidazole and the metal species may be provided in a molar ratio of Im:M of about 7:1. Advantageously, at this optimal molar ratio, a coating may be prepared comprising projections having the dimensions disclosed herein.

The coating may be obtained by or obtainable from reacting a solution containing 2-methylimidazole and the metal species in a molar ratio of about 7:1, to thereby form a coating comprising a zeolitic imidazolate framework (ZIF).

The metal salt solution may be added before, after or at the same time as the imidazole solution. In an embodiment, the metal salt solution may be added to the imidazole solution continuously in a drop-wise manner. Advantageously, as the metal species added is of a smaller molar ratio than the imidazole, the reaction may be suitably controlled.

The reaction may be undertaken under physical agitation selected from sonication, shaking, oscillation, stirring or a combination thereof.

The reaction may be undertaken at room temperature for a period of 2 to 4 hours.

In an embodiment, the reaction is undertaken for a period of about 3 hours.

Accordingly, an array of projections of a metal-organic framework, wherein each projection has at least one tapered distal end, may be obtained on a substrate surface. The array of projections may have a configuration that confers the disclosed coating with bactericidal or antimicrobial properties. The bactericidal or antimicrobial properties may utilize a physical mechanism for microbial killing, rather than a chemical mechanism, which advantageously avoids the development of microbial resistance. Without being bound by theory, it is postulated that the topography of the disclosed coating (in particular its array of tapered or pointed projections) is capable of damaging or puncturing cell membranes or cell walls of microorganisms which come into contact with a surface coated with the coating layer described herein. It is further postulated that the topography of the coating layer as disclosed herein may substantially or completely prevent cell adhesion on the coated surface.

Each projection as disclosed herein comprises a body extending from a surface, the body being substantially planar and having uniform or non-uniform width, and ending with at least one shoulder. The distal end of the disclosed projection may taper in width from the shoulder to end in a pointed apex. The shoulder of the projection may be randomly directed, that is, the planar face of the projection may be randomly facing. Each projection may comprise one, two, three, four, five or more tapered distal ends or pointed distal apices.

The projection may be two-dimensional or three-dimensional.

The projection may possess a width in the micrometer or nanometer range. The width of each projection may be from about 0.1 to 5 µm. The width of each projection may be about 0.1, 0.25, 0.5, 0.75, 1.0, 1.25, 1.5, 1.75, 2.0, 2.5, 3.0, 3.5, 4.0, 4.5, or 5.0 µm. The width of each projection may be in a range having an upper and lower limit selected from any two of the aforementioned values. In a preferred embodiment, the projection may possess a width of about 0.5 µm to 1 µm, 0.7 µm to 1 µm, 0.7 µm to 0.9 µm or 0.8 µm.

The projection may possess a height in the micrometer or nanometer range. In embodiments, the projection may be of a height greater than or equal to 1 micron. The height of each projection may be from about 1.0 to about 2.5 µm. The height of each projection may be selected from 1.0. 1.1, 1.2, 1.3, 1.4, 1.5, 1.6, 1.7, 1.8, 1.9, 2.0, 2.1, 2.2, 2.3, 2.4, or 2.5 µm. The height of each projection may be in a range having an upper and lower limit selected from any two of the aforementioned values. In an embodiment, the projection may be of a height of from about 2.0 to 2.4, 2.0 to 2.3, 2.0 to 2.2 or 2.0 to 2.1 µm. In a preferred embodiment, the projection may be of a height of from about 1.3 µm to 1.7 µm, 1.3 µm to 1.6 µm, 1.4 µm to 1.6 µm or 1.5 µm.

The projection may possess a thickness in the micrometer or nanometer range. The thickness of each projection may be from about 0.05 to about 0.25 µm. The thickness of each projection may be about 0.05, 0.075, 0.10, 0.125, 0.150, 0.175, 0.200, 0.225, or 0.250 µm. The thickness of each projection may be in a range having an upper and lower limit selected from any two of the aforementioned values. In an embodiment, the projection may have a thickness of about 0.10 to 0.20, 0.12 to 0.20, 0.14 to 0.20, 0.16 to 0.20, or about 0.18 to 0.20 µm. In a preferred embodiment, the projection may have a thickness of about 0.08 µm to 0.12 µm, 0.08 µm to 0.11 µm, 0.09 µm to 0.11 µm or 0.1 µm.

The tapered distal end of the projection may be of micrometer or nano-meter dimensions. That is, the height of the distal end, measured from the shoulder of the projection to the apex of the distal end, may be of micrometer or nano-meter dimensions. In embodiments, the height of each tapered distal end may be about 0.5, 0.45, 0.4, 0.35, 0.3, 0.25, 0.2, 0.15, 0.1, 0.05, 0.04, 0.03, 0.02, or 0.01 µm. The height of each tapered distal end may be in a range having an upper and lower limit selected from any two of the aforementioned values. In an embodiment, the height of the projection may be two, three, four, five, six, seven, eight, nine or ten times the height of the tapered distal end.

The width of the projection may be two or more, three or more, four or more, five or more, six or more, seven or more, eight or more, nine or more, or 10 or more times of the thickness of the projection.

The height of the projection, measured from the surface from which the projection extends to the apex of the distal end of the projection, may have about the same dimension as the width of the projection. In another embodiment, the height of the projection may be about 0.2, 0.3, 0.4, 0.5, 0.6, 0.7, 0.8, or 0.9 times of the width of the projection. In yet another embodiment, the height of the projection may be one or more, two or more, three or more, four or more, five or more, six or more, seven or more, eight or more, nine or more, 10 or more, 11 or more, 12 or more, 13 or more, 14 or more, 15 or more, 16 or more, 17 or more, 18 or more, 19 or more, or 20 or more times of the width of the projection.

The height, width and thickness of each projection may vary from another projection in the array, but are all within the dimensions disclosed herein.

In a preferred embodiment, the projection may have a height of about 1.5 μm, a width of about 0.8 μm and a thickness of about 0.1 μm. Advantageously, the coating having a topography comprising an array of projections having the disclosed dimensions possess optimal antimicrobial or bactericidal effects.

The pitch of the projections may vary in the array, but each projection may be spaced less than about 2 μm apart, or about 1.8 μm apart, about 1.6 μm apart, about 1.4 μm apart, about 1.2 μm apart, about 1 μm apart, about 0.8 μm apart, about 0.6 μm apart, or from about 0.5 μm to about 2 μm apart, or in a range having an upper and lower limit selected from any two of the aforementioned values.

It is known that the wing of the cicada (*Psaltoda claripennis*) comprises an array of pillar-shaped projections, each pillared projection having a height of about 200 nm. The distal end of the pillared projection of the cicada wing comprises a spherical cap of about 60 nm in diameter or width. In contrast, the height of the disclosed projection may advantageously be about 1 μm or more, while the distal end of the disclosed projection is pointed. Micrographs of the nano-pillar array structure of the cicada wing and the nano-sword array structure of the disclosed coating are shown in FIG. 8a and FIG. 8b, respectively.

More importantly, it is known that the cicada wing kills bacteria via physical interaction. Accordingly, the disclosed array of projections, being taller and sharper than the array of the cicada wing, may be advantageously more effective as an antimicrobial than that of the cicada wing. Without being bound by theory, the increase in antimicrobial activity compared to that of the cicada wing is due to the tapered distal end of the disclosed zeolitic structure exerting higher pressure on any microbial cell that comes into contact with the disclosed coating, thereby piercing through the cell membrane more easily, causing cell deformation and lysis.

The disclosed coating may be deposited on, supported on or coupled to any suitable substrate surface.

The disclosed coating may be deposited on, supported on or coupled to a surface of varying smoothness. The disclosed coating may be deposited on a smooth surface, such as glass and metal, or an uneven surface, such as wood and synthetic fiber. In embodiments, the substrate may be a biocompatible polymer and thus may advantageously be used within an animal or human body for antimicrobial purposes. In embodiments, the substrate may generally be made of metal, plastic, wood or glass materials. In embodiments, the substrate may be polymethylmethacrylate (PMMA), silicone, filter paper, copper foil, glass, synthetic fiber, disposable face-masks, polytetrafluoroethylene (Teflon) tape or wood.

In yet other embodiments, the disclosed coating may be deposited on, supported on or coupled to a surface of varying hydrophilicity. The disclosed coating may be deposited on a hydrophilic surface, characterized by having a water contact angle of about <10°, such as cellulose fiber. The disclosed coating may be deposited on a hydrophobic surface, characterized by having a water contact angle of from about >150° to >170°, such as Teflon.

The disclosed coating may be weakly soluble in aqueous solvents such as water, Tryptic Soy broth (TSB) and phosphate-buffered saline (PBS).

Advantageously, the disclosed coating may be versatile in its application and may confer antimicrobial or bactericidal properties on a variety of substrates and of a variety of materials.

Exemplary, non-limiting embodiments of a method of coating a substrate with a zeolitic imidazolate framework (ZIF) layer will now be disclosed.

In an embodiment, there is provided a method of coating a substrate with a layer of metal-organic framework having a zeolitic structure, the method comprising the steps of:
 a. providing an aqueous solution comprising an organic ligand;
 b. contacting at least a surface of the substrate with the solution; and
 c. reacting the organic ligand with a multivalent metal species to thereby deposit the metal-organic framework layer on the surface of the substrate.

In an example, there is provided a method of coating a substrate with a zeolitic imidazolate framework (ZIF) layer, the method comprising the steps of:
 a. providing an aqueous solution comprising an imidazole, imidazole derivative, imidazolate or substituted imidazolate;
 b. contacting at least a surface of the substrate with the solution; and
 c. reacting the imidazole, imidazole derivative, imidazolate or substituted imidazolate with a multivalent metal species to thereby deposit the zeolitic imidazolate framework layer on the surface of the substrate.

Advantageously, the disclosed coating method provides an economical and scalable method to prepare coatings having a topography comprising an array of projections, each projection having at least one tapered distal end. Advantageously, the disclosed coating method provides a novel approach to grow ZIF arrays of swords or flakes or leaves on substrate surfaces to confer superior microbicide and antimicrobial activity. The disclosed coating method provides a novel approach to grow ZIF arrays of projections, each projection having at least one tapered distal end, on substrate surfaces to confer superior microbicide and antimicrobial activity. The approach is simple and suitable for a wide range of substrates.

The substrate may be one as disclosed herein.

The aqueous solution may comprise an imidazole, imidazole derivative, imidazolate or substituted imidazolate (collectively referred to as imidazole) as disclosed herein.

The multivalent metal species may be selected from one or several as disclosed herein. The multivalent metal species may be in the form of a salt solution as disclosed herein.

That is, the reaction mixture may comprise a salt solution of the multivalent metal species.

The reaction step may be undertaken under conditions as disclosed herein. For example, the reaction step may be undertaken at a temperature and duration as disclosed herein. The imidazole and metal species may be provided in a molar ratio of Im:M as disclosed herein.

In embodiments, there is provided a method of preparing a disinfectant, antiseptic or an antibiotic, comprising coating a surface of a substrate with a coating as described herein. For example, the disinfectant may be used for cleaning; the antiseptic may be used on wounds; and the antibiotic may be administered to treat microbial infections.

In embodiments, there is provided the use of a ZIF as defined herein in the manufacture of a medicament for disinfection, as an antiseptic, or for sterilization. The ZIF may be formulated on or with a pharmaceutically acceptable excipient or carrier.

In embodiments, there is provided an antimicrobial surface comprising a coating as described herein. Advantageously, the coating exhibits bactericidal and antimicrobial properties against a broad spectrum of microbial strains. For example, the coating may exhibit bactericidal properties against gram-negative bacteria such as *Escherichia coli* and *Pseudomonas aeruginosa*, as well as gram-positive bacteria such as *Staphylococcus aureus*. The coating may also exhibit antimicrobial activities against fungi such as *Candida albicans*, yeast.

The coating may provide a log reduction of at least 4 to 8, or 4, 5, 6, 7, or 8 in microbial population in 24 hours when evaluated using a JIS Z 2801/ISO 22196 method.

The coating may provide a log reduction of 4, 5, 6, 7, or 8 in a microbial population having an optical density ($OD_{600}$) of 0.07.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIGS. 1a to 1h show field emission scanning electron micrographic images of glass surfaces coated with 2-methylimidazole (2-Me-Im) and Zn at different 2-Me-Im:Zn ratios, according to Example 1. FIG. 1i shows the x-ray diffraction patterns of ZIF powders produced from 2-Me-Im:Zn ratios of 35:1 and 7:1, according to Example 1. FIG. 1j shows the x-ray diffraction patterns of ZIF powder produced from a 2-Me-Im:Zn ratio of 7:1 (ZIF-L powder), ZIF-L coated glass and uncoated glass, according to Example 1.

FIG. 2a illustrates the similarity of the nano-crystals of FIG. 1b with a sword shape, while FIG. 2b shows field emission scanning electron micrographs of the top and side views of FIG. 1b.

FIG. 3 shows field emission scanning electron micrographic images of various surfaces coated with a 2-Me-Im:Zn ratio of 7:1, according to Example 2.

FIG. 4 illustrates the antimicrobial property of a PMMA surface coated with ZIF-L against *E. coli*, *S. aureus* and *C. albicans*, demonstrated in Example 3.

FIG. 5a illustrates the antimicrobial property of a glass surface coated with ZIF-L against *E. coli* in static conditions, demonstrated in Example 3. FIG. 5b illustrates the antimicrobial property of a glass surface coated with ZIF-L against *S. aureus* in static conditions, demonstrated in Example 3.

FIG. 6 illustrates the antimicrobial property of a glass surface coated with ZIF-L against *E. coli* under dynamic condition, demonstrated in Example 3.

FIG. 7a illustrates the leaching test set-up conducted in Example 4. FIG. 7b shows the leaching results when *E. coli* was grown in contact with Tryptic Soy broth (TSB) supernatant, ZIF-L supernatant and a known antimicrobial reagent IBN-C8.

FIG. 8a shows a field emission scanning electron micrographic image of the nano-pillar array structure of the cicada wing, while FIG. 8b shows a field emission scanning electron micrographic image of the nano-sword array structure of the disclosed coating.

EXAMPLES

Non-limiting examples of the invention and a comparative example will be further described in greater detail by reference to specific Examples, which should not be construed as in any way limiting the scope of the invention.

Example 1

A zeolitic imidazolate framework (ZIF) was grown directly on normal glass surfaces with 2-methylimidazole (2-Me-Im) as the organic ligand and Zn as the metal.

The glass surface was placed vertically in a reaction container containing 200.0 ml aqueous solution of 2-Me-Im (0.35 mol/L). 20.0 ml $Zn(NO_3)_2$ aqueous solution (0.5 mol/L at a 2-Me-Im:Zn molar ratio of 7:1) was introduced dropwise into the solution. The mixture was stirred at 25° C. for 3 h to obtain a continuous ZIF-L layer. The ZIF-L coated support was washed with ethanol several times to remove any loose powder on the surface. The washed coated support was then dried in an oven at 60° C.

Surface morphology of the coated surface was investigated using field emission scanning electron microscopy (SEM, JEOL JSM-7400F, Japan) with samples sputter-coated with a 2- to 3-nm layer of platinum to provide a conductive surface.

The example was repeated with different ratios of 2-Me-Im to Zn—2:1, 35:1 and 70:1.

ZIF coatings on the glass surfaces were produced and the field emission scanning electron micrographic images of the coated surfaces are shown in FIG. 1.

FIG. 1a shows the top view of the coated surface at a 2-Me-Im:Zn ratio of 2:1, while FIG. 1e shows the side view of this coated surface.

FIG. 1b shows the top view of the coated surface at a 2-Me-Im:Zn ratio of 7:1, while FIG. 1f shows the side view of this coated surface.

FIG. 1c shows the top view of the coated surface at a 2-Me-Im:Zn ratio of 35:1, while FIG. 1g shows the side view of this coated surface.

FIG. 1d shows the top view of the coated surface at a 2-Me-Im:Zn ratio of 70:1, while FIG. 1h shows the side view of this coated surface.

As shown in FIGS. 1a to h, different ratios of 2-Me-Im/Zn gave very different coating morphologies on the surface of glass. When the 2-Me-Im/Zn ratio was greater than 35 (FIGS. 1c, 1d, 1g and 1h), a continuous dense layer of ZIF coating was formed and was further confirmed to be of a ZIF-8 structure.

When the 2-Me-Im/Zn ratio was between 4 and 20, and specifically 7 (FIGS. 1b and 1f), a continuous layer of an array of nano-sword projections was formed and was further confirmed to be of a ZIF-L structure. That is, sword-shaped nano-crystals grew closely on top of the glass surface, with the sharp end of the crystals facing upwards, although their shoulders were randomly directed. This is shown in FIG. 2, which illustrates the top and side views of FIG. 1b.

Distances between the nano-swords projecting from the glass surface were also irregular, but were all less than 2 μm.

The x-ray diffraction patterns of ZIF powders produced from 2-Me-Im:Zn ratios of 35:1 and 7:1 are shown in FIG. 1i. It can be seen that the different ratios produce diffraction patterns with intensities that differ for similar 2θ values.

The x-ray diffraction patterns of ZIF powder produced from a 2-Me-Im:Zn ratio of 7:1 (ZIF-L powder), ZIF-L coated glass and uncoated glass are shown in FIG. 1j.

Example 2

The steps in Example 1 were repeated for a 2-Me-Im:Zn ratio of 7:1 (resulting in ZIF-L structures), except the surfaces used in this example were varied. In addition to glass as in Example 1, the surfaces used in this example were poly(methyl methacrylate) (PMMA), silicone, filter paper, metal (copper foil), synthetic cellulose fiber (from a disposable face-mask), Teflon tape and wood.

It was found that ZIF-L could be successfully grown on all of these surfaces. The ZIF-L coatings on these surfaces have similar nano-sword array structures, although with some variations in the array density.

This is shown in the series of field emission scanning electron micrograph images in FIG. 3. The inset in each of the series of images in FIG. 3 shows the magnified view of the coated substrates. Specifically, FIG. 3a shows ZIF-L nano-sword arrays on PMMA, FIG. 3b shows ZIF-L nano-sword arrays on silicone, FIG. 3c shows ZIF-L nano-sword arrays on glass, FIG. 3d shows ZIF-L nano-sword arrays on filter paper, FIG. 3e shows ZIF-L nano-sword arrays on copper foil, FIG. 3f shows ZIF-L nano-sword arrays on synthetic fiber (from face-mask), FIG. 3g shows ZIF-L nano-sword arrays on Teflon tape and FIG. 3h shows ZIF-L nano-sword arrays on wood.

Therefore, this example shows that ZIF-L could be successfully grown on surfaces made of different materials, such as metal, plastic, wood and glass.

In addition, this example shows that ZIF-L could be successfully grown on surfaces having various degrees of hydrophilicity, ranging from cellulose fiber which has the highest hydrophilicity (water contacting angle <10° C.) to Teflon which has the highest hydrophobicity (water contacting angle >170° C.).

This example also shows that ZIF-L could be successfully grown on surfaces having various degrees of smoothness, ranging from smooth surfaces such as glass and Teflon to rough surfaces such as filter paper and wood.

Importantly, all these ZIF-L nano-array coated surfaces demonstrated strong bactericidal property. Therefore, these results demonstrate that the ZIF-L nano-sword array coating approach is versatile and this simple coating method can be applied to various supports.

Example 3

In this example, the bactericidal performance of a ZIF-L coated poly(methyl methacrylate) (PMMA) surface against Gram-negative bacteria *Escherichia coli* (ATCC 8739), Gram-positive bacteria *Staphylococcus aureus* (ATCC 6538) and the yeast fungus *Candida albicans* (ATCC 10231) was tested.

All bacteria and yeast were stored frozen at −80° C., and were grown overnight at 37° C. in Tryptic Soy broth (TSB) prior to experiments. Yeast was grown overnight at 22° C. in Yeast Mold (YM) broth. Subsamples of these cultures were grown for 3 h further and diluted to give an optical density value of 0.07 at 600 nm, corresponding to approx. $3 \times 10^8$ CFU mL$^{-1}$ (MacFarland's Standard).

The steps in Example 1 were repeated, except the surface used in this example was a PMMA surface.

The antimicrobial property of the coated PMMA surface was evaluated using the JIS Z 2801/ISO 22196 method. Briefly, exponentially growing bacteria with OD600=0.07 was further diluted 100 times and used as test inoculum. A hundred and fifty microliters were inoculated onto each samples and then covered with a 40 mm square of plastic film to ensure close contact between the culture and the coating. The samples were placed in 90-mm-diameter petri dishes and incubated at 37° C. After 24 h, both the coated samples and controls and cover films were carefully washed with 14.85 ml of cold TSB to re-suspend the bacteria. A viability count was performed by dilution and plating on growth medium agar plates in duplicate and incubation overnight at 37° C. Since zero cannot be plotted on logarithmic scale, one was added to each count when no colony was observed to allow plotting zero counts.

The results are shown in the graphs of FIG. 4 and evidence the antimicrobial property of a PMMA surface coated with ZIF-L.

It was found that the ZIF-L nano-sword array, when a 2-Me-Im:Zn ratio of 7:1 was used, was strongly bactericidal against *E. coli* with a log reduction of 7 in 24 hours. As shown in FIG. 4a, the CFU graph of the 7:1 ratio which resulted in the ZIF-L nano-sword projections has negligible *E. coli* CFU readings, while the other CFU graphs of the 2:1 ratio, the 35:1 ratio, the 70:1 ratio and the control PMMA surface with no coating have *E. coli* CFU readings of 10$^7$ or more. Furthermore, it can be seen from the CFU graphs of the 35:1 ratio and the 70:1 ratio that the ZIF-8 dense coatings were non-bactericidal.

FIG. 4b shows the 51-day progression of *E. coli* growth on the control PMMA surface with no coating compared with the PMMA surface coated with ZIF-L. It can be seen that ZIF-L coated PMMA effectively killed *E. coli* with a log reduction of more than 7 throughout the 51 days. Further, the negligible *E. coli* CFU readings throughout all 51 days indicate good stability of the ZIF-L nano-sword coated surface.

FIG. 4c shows the 24-hour progression of *S. aureus* growth on the control PMMA surface with no coating compared with the PMMA surface coated with ZIF-L. It can be seen that ZIF-L coated PMMA effectively killed *S. aureus* with a log reduction of 8, resulting in negligible *S. aureus* CFU readings after 24 hours.

FIG. 4d shows the 24-hour progression of *C. albicans* growth on the control PMMA surface with no coating compared with the PMMA surface coated with ZIF-L. It can be seen that ZIF-L coated PMMA effectively killed *C. albicans* with a log reduction of 4 after 24 hours.

Therefore, these results demonstrate that the ZIF-L nano-sword array coating approach is highly bactericidal and can efficiently kill a broad spectrum of bacterial strains.

This example was repeated again to determine the bactericidal performance of a ZIF-L coated glass surface against Gram-negative bacteria *Escherichia coli* (ATCC 8739) and Gram-positive bacteria *Staphylococcus aureus* (ATCC 6538).

The method used to determine bactericidal kinetics was as follows. Bacteria were grown to log phase in TSB and re-suspended in PBS. After adjusting to OD600=0.07, the re-suspended cells were further diluted 10 times. Then 3 ml of the cell suspension was added to the well of a 6-well plate in triplicates with each well containing a 5.2 cm² area ZIF-L coated glass sample or plain glass sample as control. The 6-well plate was incubated at 37° C. under constant shaking of 150 rpm. At each time point (0.5, 1, 3 and 6 h), 100 µl of the cell suspensions were removed, rescued by a series of 10-fold dilutions with growth medium, and kept on ice until plating. For plating, 100 µl of the diluted samples were spread on growth medium agar plates and colonies were counted after overnight incubation at 37° C.

The results are shown in the graphs of FIG. 5 and FIG. 6 and evidence the antimicrobial property of a glass surface coated with ZIF-L.

As shown in FIG. 5a and FIG. 5b, the CFU graphs of the 2-Me-Im:Zn ratio of 7:1 which resulted in the ZIF-L nano-sword projections evidence negligible *E. coli* and *S. aureus* CFU readings, respectively, in 24 hours and under static condition when compared to the control glass surface with no coating.

As shown in FIG. 6, the killing kinetics in terms of CFU evidence negligible *E. coli* after 24 hours at 37° C. in PBS under dynamic condition (i.e. with constant shaking speed of 150 rpm) for the glass coated with ZIF-L when compared to the control glass surface with no coating.

It is therefore evident that ZIF-L has a lower MIC than ZIF-8. Therefore, a lower concentration of ZIF-L is required to inhibit *E. coli, S. aureus* and *C. albicans* as compared to ZIF-8.

The solubilities of ZIF-L in $H_2O$, phosphate-buffered saline (PBS) and Tryptic Soy broth (TSB) (37° C., 24 hours) are 4.6, 316 and 3.6 ppm of Zn concentration respectively, which are far less than its MIC value (5000 ppm). This indicates that the bactericidal effect came from the ZIF-L coating itself and not the leached Zn. This also indicates that the concentration of Zn that leached from the ZIF-L coating into the various solvents is negligible as compared to the concentration of ZIF-L needed to inhibit *E. Coli*.

To further exclude the chemical effect from Zn in the bactericidal performance of the ZIF-L nano-sword array, a Pt-coated nano-sword array was prepared and it demonstrated similar bactericidal property against *E. coli*. Together with the fact that ZIF-8 dense coating surfaces are non-bactericidal, it was concluded that the bactericidal property of ZIF-L nano-sword coated surfaces relies on physical mechanisms rather than biochemical mechanisms.

A further Zn leaching test was conducted as follows. 5 mg/ml ZIF-L in TSB was incubated at 37° C. for 24 h. After centrifugation, 100 µl of the supernatant was inoculated in a hole of 1×1 cm² carved in agar plates previously seeded with a confluent layer of *E. coli* (see FIG. 7a). The plates were incubated at 37° C. for 24 h, and the presence or absence of inhibition halos was used to assess potential leaching of zinc ions.

The test was repeated with TSB supernatant and a known solution of antimicrobial reagent IBN-C8 (structure below) at 64 µg/ml.

IBN-C8

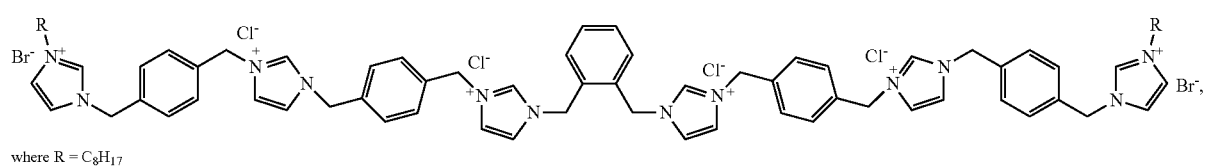

where $R = C_8H_{17}$

Example 4

This example was conducted to prove the hypothesis that ZIF-L nano-sword coated surfaces kill bacteria exclusively via physical interaction.

A set of control experiments were conducted with ZIF-L and ZIF-8 powders to prove this hypothesis. The minimal inhibitory concentration (MIC) of ZIF-L powders synthesized from a solution with a 2-Me-Im:Zn ratio of 7:1 was tested against *E. coli, S. aureus* and *C. albicans*. The same test was conducted for ZIF-8 powders, 2-Me-Im alone and $Zn(NO_3)_2 \cdot 4H_2O$ alone. The MIC values in mg/mL are tabulated below.

TABLE 1

|  | *E. coli* | *S. aureus* | *C. albicans* |
| --- | --- | --- | --- |
| 2-Me-Im | 12.5 | 25 | 6.2 |
| $Zn(NO_3)_2 \cdot 4H_2O$ | 3.1* | >50* | 0.8 |
| ZIF-L | 2.5 | 2.5 | 1.2 |
| ZIF-8 | >5.0 | >5.0 | 5.0 |

*The tested chemical formed precipitate in Tryptic Soy broth (TSB) medium.

As shown in FIG. 7b, inhibition of *E. coli* (indicated by the arrow pointing to an inhibition halo around the 1×1 cm² hole) was detected only in the sample with IBN-C8. Inhibition of *E. coli* was not detected when *E. coli* cells were grown in contact with ZIF-L supernatant.

INDUSTRIAL APPLICABILITY

The disclosed coating may be grown or prepared directly on a surface of a substrate to be coated. Substrate that can be coated may be made of a wide variety of materials and may have a wide variety of properties.

The disclosed method of coating the substrate may be simple, economical and scalable. The disclosed method is a novel approach to grow ZIF nano-arrays on surfaces to confer the surface with superior microbicide activity.

The antimicrobial effect of the disclosed coating is due to a physical microbicidal mechanism, rather than by biochemical reactions. Advantageously, the development of microbial resistance may be avoided. Further advantageously, the disclosed microbicide surfaces may be clean and safe to the user and require no external microbicidal chemicals.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A method of killing or inhibiting the growth of a microorganism, said method comprising:
    contacting said microorganism with a coating composition, wherein the coating composition comprises a topography having an array of projections formed of a zeolitic imidazolate framework (ZIF),
    wherein the ZIF comprises at least one multivalent metal species and at least one organic ligand,
    wherein each projection has at least one tapered distal end, and
    wherein said projections possess a height greater than or equal to 1 micron.

2. The method of claim 1, wherein said multivalent metal species is tetrahedrally coordinated with said organic ligand.

3. The method of claim 1, wherein said multivalent metal species is selected from the group consisting of divalent, trivalent, and tetravalent metal species from the d-block Groups 3-12 of the Periodic Table of Elements, and mixtures thereof.

4. The method of claim 1, wherein said organic ligand is an imidazole, an imidazole derivative, an imidazolate or a substituted imidazolate.

5. The method of claim 1, wherein said organic ligand is derived from an imidazole having the following structure:

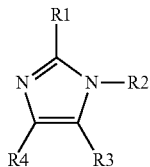

R1 is $C_{1-10}$ alkyl, $C_{2-10}$ alkenyl, $C_{3-10}$ cycloalkyl, or phenyl;
R2 is H; and
each R3 and R4 are independently H, $C_{1-10}$ alkyl, $C_{2-10}$ alkenyl, $C_{3-10}$ cycloalkyl, or phenyl;
wherein each of R1, R3 and R4 is optionally substituted with halogen, amino, hydroxy, $C_{1-10}$ alkyl, oxo, cyano, nitro, $C_{1-10}$ haloalkyl, $C_{1-10}$ alkoxy and $C_{1-10}$ haloalkoxy.

6. The method of claim 1, wherein said organic ligand is derived from the compound:

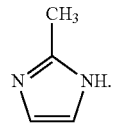

7. The method of claim 1, wherein said projections are spaced less than 2 µm apart or possess a width from about 0.1 to 5 µm.

8. The method of claim 1, wherein the coating composition is coupled to a substrate surface.

9. The method of claim 8, wherein the ZIF is prepared by contacting the substrate surface with a reaction mixture comprising said organic ligand and said multivalent metal species.

10. The method of claim 9, wherein said organic ligand is an imidazole, an imidazole derivative, an imidazolate or a substituted imidazolate.

11. The method of claim 9, wherein said organic ligand is 2-methylimidazole.

12. The method of claim 9, wherein said multivalent metal species is Zn.

13. The method of claim 10, wherein said organic ligand (Im) and said multivalent metal species (M) are provided in a molar ratio of Im: M of between 4:1 and 20:1.

14. The method of claim 13, wherein the molar ratio of Im: M is 7:1.

15. The method of claim 1, wherein the ZIF has a ZIF-L crystal structure.

16. The method of claim 1, wherein the microorganism is selected from the group consisting of gram-positive bacteria, gram-negative bacteria and fungi.

17. The method of claim 16, wherein the gram-positive bacteria is *Staphylococcus aureus*.

18. The method of claim 16, wherein the gram-negative bacteria is *Escherichia coli* or *Pseudomonas auruginosa*.

19. The method of claim 16, wherein the fungi is *Candida albicans*, yeast.

20. The method of preparing a disinfectant, antiseptic or an antibiotic comprising coating a surface of a substrate with a coating composition, comprising a topography having an array of projections formed of a zeolitic imidazolate framework (ZIF), wherein the ZIF comprises at least one multivalent metal species and at least one organic ligand, wherein each projection has at least one tapered distal end, and wherein said projections possess a height greater than or equal to 1 micron.

* * * * *